United States Patent
Kumar et al.

(10) Patent No.: US 6,524,618 B1
(45) Date of Patent: Feb. 25, 2003

(54) DIRECTLY COMPRESSIBLE EXTENDED-RELEASE MATRIX FORMULATION FOR METFORMIN HYDROCHLORIDE

(76) Inventors: Vijai Kumar, 67 Whitewood Dr., Morris Plains, NJ (US) 07950; Kevin Scott McGuffy, 11 River Rd., Stanhope, NJ (US) 07874

(*) Notice: Subject to any disclaimer, the term of this patent is extended or adjusted under 35 U.S.C. 154(b) by 37 days.

(21) Appl. No.: 09/879,748

(22) Filed: Jun. 12, 2001

(51) Int. Cl.[7] ............................. A61K 9/14; A61K 9/22; A61K 9/26
(52) U.S. Cl. ................. 424/468; 424/465; 424/469; 424/486; 424/488; 424/489; 514/772.3; 514/770; 514/777; 514/781; 514/866; 514/965; 514/951
(58) Field of Search ................................ 424/465, 468, 424/469, 484, 486, 488, 489

(56) References Cited

U.S. PATENT DOCUMENTS

| 4,404,183 A | 9/1983 | Kawata et al. ................ 424/19 |
| 4,649,043 A | 3/1987 | Urquhart et al. ............. 424/469 |
| 4,661,521 A | 4/1987 | Salpekar et al. ............. 514/613 |
| 4,690,822 A | 9/1987 | Uemura et al. ............. 424/455 |
| 4,816,263 A | 3/1989 | Ayer et al. ................... 424/468 |
| 4,834,985 A | 5/1989 | Elger et al. ................. 424/488 |
| 5,055,306 A | 10/1991 | Barry et al. ................ 424/482 |
| 5,645,858 A | 7/1997 | Kotwal et al. ............... 424/495 |
| 5,733,578 A | 3/1998 | Hunter et al. ............... 424/489 |
| 5,955,106 A | 9/1999 | Moeckel et al. ............ 424/464 |
| 6,117,451 A | 9/2000 | Kumar ....................... 424/465 |
| 6,340,475 B2 * | 1/2002 | Shell et al. ................. 424/469 |

FOREIGN PATENT DOCUMENTS

| EP | 0 609 961 A1 | 8/1994 | ......... A61K/31/485 |
| WO | WO99/47128 | 9/1999 | ............ A61K/9/24 |

* cited by examiner

Primary Examiner—James M. Spear
(74) Attorney, Agent, or Firm—Jack Matalon

(57) ABSTRACT

An extended-release matrx formulation capable of being directly compressed into tablets comprising metformin hydrochloride blended with specific excipients. The excipients used in the formulation enhance the flow and compaction properties of the drug and insure that the formulation is directly compressible into a tablet containing about 100 mg to about 800 mg, preferably about 250 mg to about 750 mg, of metformin hydrochloride in unit dosage form. Each tablet produced by direct compression of the formulaton has the desired hardness and dissolution characteristics such that the drug is released in the body of the subject over an extended period of time.

20 Claims, No Drawings

DIRECTLY COMPRESSIBLE EXTENDED-RELEASE MATRIX FORMULATION FOR METFORMIN HYDROCHLORIDE

FIELD OF THE INVENTION

The invention relates to a directly compressible extended-release matrix formulaton containing N,N-dethyl-imidodicaboimdic diarnide hydrochloride (hereinafter referred to as "metformin hydrochlorido" or "metformin HCl"). The formulaton is prepared in the form of a tableting powder which is capable of being directly compressed into metformin HCl tablets. The invention also relate to a process for preparing extended-release metformin HCl tablets by blending the drug with specific excipients and therefore directly compressing the blend into tablets.

BACKGROUND OF THE INVENTION

Metformin is an antihyperglycemic agent of the bigande elms used in the treatment of non-insulin dependent diabetes mellitus ("NIDDM"). It is usually marketed in the form of its hydrochloride salt as Glucophage®. Metformin hydrochloride is hygroscopic and somewhat unstable. Moreover, metformin hydrochloride is not inherently compressible and thus presents formulation problems.

Metformin hydrochloride has intinsically poor permeability in the lower portion of the gastrointestinal tract leading to absorption almost exclusively in the upper part of the gastrointestinal tract. Its oral bioavailability is in the range of 40 to 60% decreasing with increasing dosage, which suggests some kind of saturable absorption process, or permeability/transit time limited absorption. It also has a very high water solubility (>300 mg/ml at 250° C.). This can lead to difficulty in providing an extended, i.e., slow, release rate from a formulation and problems in controlling the initial burst of drug from such a formulaton. These two difficulties are further compounded by the high unit dose, about 500 mg to about 750 mg per tablet, usually required for metformin hydrochloride to provide optimal dosing.

Drugs with very high solubility in water (for example, greater than 100 mg/ml) can be difficult to formulate into a controlled release oral dosage form. Solubility is a driving force for a drug substance to dissolve in water; the greater the solubility the greater the rate of dissolution when all other factors are maintained constant.

In a controlled release dosage form, the formulator tries to reduce the rate of dissolution by, for example, embedding the drug in a polymeric matrix or surrounding it with a polymeric barrier membrane through which drug must diffuse to be released for absorption To reduce the rate of release of drug from the dosage form to an appropriate level consistent with the blood level profile desired for a drug possessing very high water solubility, very large amounts of polymer would be required for the matrix or Per membrane. If the total daily dose of drug to be delivered is of the order of only a few milligrams this may be feasible, but many drugs having the solubility properties described require total daily doses of the order of many hundreds of milligrams. Whilst it is possible to create oral controlled release dosage forms for such products by use of large amounts of polymer, however, this leads to an unacceptably large dosage form.

A further problem with highly water soluble drugs formulated into a controlled release dosage form is that a significant and variable burst of the drug can occur from these systems. The burst of a highly water-soluble drug is the initial rapid release of drug that occurs from oral controlled release dosage forms when first contacting fluid, such as gastric fluids, prior to release controlling mechanisms of the dosage form establishing themselves and a stable release rate being provided. Hydration of any polymer matrix used to formulate the dosage form is a prerequirement of establishing a stable release rate. Thus, a readily hydrating polymer is required to establish the desired stable release rate. However, if the polymer used is slow to hydrate, then an undesirable variable burst can occur.

The three processes for making compressed tablets are wet granulation, direct compression and dry granulation (slugging or roller compaction). The method of preparation and type of excipients are selected to give the tablet formulation the desired physical characteristics that allow for the rapid compression of the tablets. After compression, the tablets must have a number of additional attributes such as appearance, hardness, disintegrating ability, and an acceptable dissolution profile. Choice of fillers and other excipients will depend on the chemical and physical properties of the drug, behavior of the mixture during processing, and the properties of the final tablets. Preformulation studies are done to determine the chemical and physical compatibility of the active component with proposed excipients.

The properties of the drug, its dosage forms, and economics of the operation will determine selection of the best process for tableting. Generally, both wet granulation and direct compression are used in developing a tablet.

The dry granulation method may be used where one of the constitutes, either the drug or the diluents, has sufficient cohesive properties to be tableted. The method consists of blending; slugg the ingredients, dry screening, lubrication, and compression. The wet granulation method is used to convert powder mixture into granules having suitable flow and cohesive properties for tableting. The procedure consists of mixing the powders in a suitable blender followed by adding the granulating solution under shear to the mixed powders to obtain a granulation The damp mass is then screened through a suitable screen and dried by tray dying or fluidized bed drying. Alternately, the wet mass may be dried and passed through a mill. The overall process includes: weighing dry powder blending, wet granulating, drying, milling, blending lubrication and compression.

In general, powders do not have sufficient adhesive or cohesive properties to form hard, strong granules. A binder is usually required to bond the powder particles together due to the poor cohesive properties of most powders. Heat and moisture sensitive drugs cannot usually be manufactured using wet granulation. The large number of processing steps and processing time are problems due to high labor and manufacturing costs.

Direct compression is regarded as a relatively quick process where the powdered materials are compressed directly without changing the physical and chemical properties of the drug. The active ingredient(s), direct compression excipients and other auxiliary substances, such as a glidant and lubricant are blended in a twin shell blender or similar low shear apparatus before being compressed into tablets. This type of mixing was believed to be essential in order to prepare pharmaceutically acceptable dosage forms. For example, Remington's Pharmaceutical Sciences ("RPS"), $17^{th}$ edition(1985), cautions pharmaceutical scientists that the manner in which a lubricant is added to a formulation must be carefully controlled. Accordingly, lubricants are usually added to a granulation by gentle mixing. RPS warns that prolonged blending of a lubricant with a granulation can materially affect hardness and disintegration time for the resulting tablets. Furthermore, Ansel et al., ("Pharmaceutical Dosage Forms and Drug Delivery Systems", 6$^{th}$ edition, pp. 199 and 213–220) indicate that excessive blending of lubricants with the granulate ingredients cause waterproofing of the granule and reduces tablet hardness or strength of the compressed tablet For these reasons, high shear mixing conditions have not been used to prepare direct compression dosage forms. The advantages of direct compression include uniformity of blend, few manufacturing steps involved, (i.e., the overall process involves weighing of powders, blending and compression, hence less cost), elimination of heat and moisture, prime particle dissociation, and physical stability.

A solid dosage form containing a high dose drug (i.e., the drug itself comprises a substantial portion of the total compressed tablet weight) could only be directly compressed if the drug itself had sufficient physical characteristics (e.g., cohesiveness) for the ingredients to be directly compressed.

Metformin HCl (an oral hypoglycemic) is considered a high dose drug Most tablet formulations include a range of 30 to 60% by weight of metformin HCl per tablet. This high dose drug, combined with its rather poor physical characteristics for direct compression, has not allowed pharmaceutical manufacturers to use direct compression as a method to prepare the final tablet.

For example, in U.S. Pat. No. 5,733,578, acetaminophen could not be directly compressed with microcrystalline cellulose to form acceptable tablets. The final product tended to be soft, prone to capping and otherwise not pharmaceutically acceptable (i.e., difficult to swallow because of the large size). Consequently, the more time consuming and expensive wet granulation technique was used.

In another patent (U.S. Pat. No. 4,661,521) on direct tableting of an acetainiophen composition, N-acetyl-paminophenol could only be directly compressed using additional steps such as slugging or roller compaction of the tableting mix The patentees employed fluidized bed apparatus for thorough blending of N-acetyl-mino phenol with pregelatinized starch High shear mixing is used to form slurry, which is dried and fluidized before sizing to achieve the appropriate particle size.

Despite the advantages of the direct compression, such as reduced processing time and cost, wet granulation is widely used in the industry to prepare solid dosage forms. Wet granulation is often preferred over direct compression because wet granulation has a greater chance of overcoming any problems associated with the physical characteristics of various ingredients in the formulation. This provides material which has the required flow and cohesive properties necessary to obtain an acceptable solid dosage form.

The popularity of wet granulation compared to direct compression is based on at least three advantages. First, wet granulation provides the material to be compressed with better wetting properties, particularly in the case of hydrophobic drug substances. Second, the content uniformity of the solid dosage form is generally improved with wet granulation because all of the granules usually containing the same amount of drug. Lastly, the segregation of drug(s) from excipients is avoided.

Segregation could be a potential problem with direct compression. The size and shape of particles comprising the granulate to be compressed are optimized through the wet granulation process. This is because when a dry solid is wet granulated the binder "glues" particles together, so that they agglomerate into spherical granules.

In spite of the advantages afforded by wet granulation, many manufacturers would welcome the opportunity to direct compress tablets containing high dose Metformin HCl. There is a need in the industry for techniques and pharmaceutical excipients which will allow manufacturers to prepare high dose Metformin HCl tablets by direct compression which will avoid the time and expense of wet granulation.

Processes are known for preparing extended-release tablets of metformin hydrochloride by the use of wet granulation due to the poor compressibility and relatively high solubility of the drug. A prior patent, U.S. Pat. No. 6,117,481, provided a formulation and process for directly compressing metformin hydrochloride through the use of particular excipients and binding agents. However, the directly compressed tablets produced by the invention disclosed in the '481 patent were not extended-release tablets.

The need exists for a drug delivery system that has a longer transit time in the stomach and acts as an in vivo reservoir that releases drug at a controlled rate continuously over a prolonged time for absorption in the stomach and the intestine. Drug is administered from a delivery system that releases the drug as it passes through the sintestinal tract Extended-release delivery systems are used because they eliminate the need for multiple dosing.

The convenience of extended-release preparations which maintain the blood concentration of the drug at a desired level over a prolonged period of time has been recognized. Extended-release preparations such as a slow-release matrix type tablet in which the ingredients are imbedded in a matrix, such as polymeric resins, release the active ingredient by diffusion and erosion.

Most extended-release forms are designed so that the administration of a single dosage unit provides the immediate release of an amount of drug that promptly produces the desired therapeutic effect and also a gradual and continual release of additional amounts of drug to maintain this level of effect over an extended period of time to overcome frequent or multiple dosing. In this type of dosage form, the design is based on the particular qualities of each individual drug. In the case of Metformin HCl, which is a very highly soluble drug, it is imperative to control the release in order to obtain a controlled release formulation.

What may be an effective type of dosage form design for one drug may be ineffective for another drug for extended release because of peculiar physical, chemical and biological qualities. To maintain a constant level of drug in the system, the drug must be released from the dosage form at a rate that will replace the amount of drug being metabolized and eliminated from the body.

Other advantages of extended-release products are reduced side effects and increased patient convenience. These advantages relate to the fact that extended-release preparations are designed to maintain the blood concentration of the drug at a desired level over a prolonged period of time thereby reducing the frequency of dosing and thus ensuring patient compliance.

OBJECTS OF THE INVENTION

It is an object of the invention to provide a directly compressible, extended-release matrix formulation for metformin hydrochloride.

It is a further object of the invention to provide a directly compressed tablet containing about 100 mg to about 800 mg metformin hydrochloride, more preferably about 250 mg to about 750 mg, in unit dosage form having an acceptable dissolution profile over an extended period of time and having an acceptable degree of hardness and resistance to chipping.

It is a further object of the invention to provide a process for the preparation of the formulation and for directly compressing the formulation into such extended-release tablets.

The foregoing objects and other objects have been attained by the present invention as will be apparent from the description which follows.

SUMMARY OF THE INVENTION

The present invention provides a directly compressible, extended-release matrix formulation for metformin hydrochloride in the form of a free-flowing powder. Tablets directly compressed from such formulation will have an acceptable dissolution profile over an extended period of time and an acceptable degree of hardness and friability.

DETAILED DESCRIPTION OF THE INVENTION

The directly compressible, extended-release matrix formulation of the present invention comprises the following ingredients:

(a) about 30 to about 60% by weight on a dry weight basis, based on the weight of the formulation, of metformin hydrochloride having a particle size of about 150 to about 600 microns and a density in the range of about 0.6 to about 0.9 g/ml;

(b) one or more pharmaceutically acceptable polymers selected from the group consisting of: (i) polyethylene oxide having a number average molecular weight of about 100,000 to about 7,000,000, a particle size of about 100 to about 900 microns, a density of about 1.15 to about 1.26 g/ml and a viscosity of about 7,500 to about 10,000 centipoise at 20° C., present in an amount of about 5 to about 45% by weight on a dry weight basis, based on the weight of the formulation; (ii) hydroxypropyl cellulose having a number average molecular weight of about 80,000 to about 1,150,000, a particle size of about 170 to about 600 microns, a density of about 3.0 to about 7.0 g/ml and a viscosity of about 300 to about 3,000 centipoise at 20° C., present in an amount of about 10 to about 35% by weight on a dry weight basis, based on the weight of the formulation; (iii) bydroxyethyl cellulose having a number average molecular weight of about 75,000 to about 1,500,000, a particle size of about 50 to about 250 microns, a density of about 0.2 to about 0.9 g/ml and a viscosity of about 3,500 to about 5,500 centipoise at 20° C., present in an amount of about 10 to about 20% by weight on a dry weight basis, based on the weight of the formulation; and (iv) ethyl cellulose having a particle size of about 1 to about 10 microns, a density of about 0.1 to about 0.8 g/ml and a viscosity of about 5 to about 15 centipoise at 20° C., present in an amount of about S to about 20% by weight on a dry weight basis, based on the weight of the formulation;

(c) about 5 to about 40%/o by weight on a dry weight basis, based on the weight of the formulation, of a pharmaceutically acceptable insoluble filler;

(d) about 0.1 to about 3% by weight on a dry weight basis, based on the weight of the formulation, of a pharmaceutically acceptable glidant; and (e) about 0.1 to about 3% by weight on a dry weight basis, based on the weight of the formulation, of a pharmaceutically acceptable lubricant.

Preferably, the filler is selected from the group consisting of pharmaceutically acceptable: (a) lactose having a particle size of about 20 to about 400 microns and a density of about 0.3 to about 0.9 g/ml; (b) dibasic calcium phosphate having a particle size of about to about 425 microns and a density of about 0.5 to about 1.5 g/ml; (c) microcrystalline cellulose having a particle size of about 20 to about 300 microns and a density of about 0.2 to about 0.7 mi; (d) calcium sulfate having a particle size of about 1 to about 200 microns and a density of about 0.6 to about 1.3 g/ml; and mixtures thereof The preferable glidant comprises colloidal silicon dioxide having a density of about 0.029 to about 0.040 g/rl.

The lubricant may be hydrophobic or hydrophilic and includes materials such as stearic acid, talc and magnesium stearate. The lubricant is quite important since it reduces the friction between the die wall and the tablet formulation during the compression and ejection of the metformin hydrochloride extended-release tablets. The lubricant also aids in the flow of the powder, i.e., the tablet formulation into the hopper and into the die and it also helps to prevent the adhesion of the tablets to the punches and the dies. The preferable lubricant comprises magnesium stearate having a particle size of about 450 to about 550 microns and a density of about 1.00 to about 1.80 g/ml.

The extended-release tablet which is prepared by directly compressing the matrix formulation described above will contain about 100 mg to about 800 mg, preferably about 250 mg to about 750 mg, of metformin hydrochloride present in unit dosage form. If desired the medicament metformin hydrochloride may be mixed with one or more other antidiabetic agents prior to direct compression of the matrix formulation. Suitable antidiabetic agents include antidiabetic agents selected from the group consisting of sulfonylureas (e.g., glyburide, glipizide, glimepiride, glipyride, chlotpop de and gliciazide), α-glucosidase inhibitors (e.g., Acarbose® and Miglitol®; and glitazones (e.g., rosiglitone and pioglitzone) as well as combinations of two or more of the foregoing antidiabetic agents.

The direct compression process for preparing the extended-release tablet containing about 100 mg to about 800 mg, preferably about 250 mg to about 750 mg, of metformin hydrochloride in unit dosage form is relatively simple and straight forward. The ingredients described above are blended for e.g., 1 to 30 minutes, under low-shear conditions using conventional blending equipment such as a Patterson Kelly "V" blender. The blended formulation is thereafter directly compressed using conventional types of tableting equipment such as round concave punches.

The following nonlimiting examples shall serve to illustrate the various embodiments of the present invention.

EXAMPLE 1

A directly-compressible formulation for an extended release tablet containing 500 mg of metformin hydrochloride was prepared by mixing the ingredients set forth in Table I, except for the lubricant and glidant, in a V-blender for 5–15 minutes at low shear conditions. The lubricant, magnesium stearate, and the glidant, colloidal silicon dioxide, were then added to the mixture and mixing was continued at low shear conditions for an additional 3–7 minutes. The formulation of Table 1 was directly compressed using a Manesty, rotary type tablet press into tablets. The tablets were monitored for weight hardness, thickness and friability. The hardness was adjusted to between 16 and 20 kp, preferably between 1 8 and 20 kp. The tablet thickness ranged from 0.275 into about 0.315 in. Friability was maintained below 1%.

TABLE I

| Ingredient | Weight (mg) |
| --- | --- |
| Metformin hydrochloride | 500.00 |
| Lactose | 240.00 |
| Hydroxypropyl cellulose | 250.00 |
| Colloidal silicon dioxide | 5.00 |
| Magnesium stearate | 5.00 |
| Total | 1000.00 |

EXAMPLE 2

Example 1 was repeated using the same mixing procedure as set forth in Example 1 with the ingredients set forth in Table II. The formulation described in Table II was directly compressed and monitored for weight, hardness, thickness and friability using the same apparatus and procedure as set forth in Example 1.

TABLE II

| Ingredient | Weight (mg) |
| --- | --- |
| Metformin hydrochloride | 500.00 |
| Lactose | 190.00 |
| Polyethylene oxide | 300.00 |
| Colloidal silicon dioxide | 5.00 |
| Magnesium stearate | 5.00 |
| Total | 1000.00 |

EXAMPLE 3

Example 1 was repeated using the same mixing procedure as set forth in Example 1 with the ingredients set forth in Table III. The formulation described in Table III was directly compressed and monitored for weight, hardness, thickness and friability using the same apparatus and procedure as set forth in Example 1.

TABLE III

| Ingredient | Weight (mg) |
| --- | --- |
| Metformin hydrochloride | 500.00 |
| Lactose | 160.00 |
| Hydroxypropyl cellulose | 330.00 |
| Colloidal silicon dioxide | 5.00 |
| Magnesium stearate | 5.00 |
| Total | 1000.00 |

EXAMPLES 4–7

Example 1 was repeated using the same procedure as set forth in Example 1 with the ingredients set forth in Tables IV–VII. The formulations described in Tables IV–VII were directly compressed and monitored for weight, hardness, thickness and friability using the same apparatus and procedure as set forth in Example 1.

TABLE IV

| Ingredient | Weight (mg) |
| --- | --- |
| Metformin hydrochloride | 500.00 |
| Dibasic Calcium Phosphate | 45.90 |

TABLE IV-continued

| Ingredient | Weight (mg) |
| --- | --- |
| Hydroxypropyl cellulose | 329.60 |
| Ethyl cellulose | 92.70 |
| Povidone | 51.50 |
| Colloidal silicon dioxide | 5.15 |
| Magnesium stearate | 5.15 |
| Total | 1030.00 |

TABLE V

| Ingredient | Weight (mg) |
| --- | --- |
| Metformin hydrochloride | 500.00 |
| Lactose | 140.00 |
| Hydroxypropyl cellulose | 350.00 |
| Colloidal silicon dioxide | 5.00 |
| Magnesium stearate | 5.00 |
| Total | 1000.00 |

TABLE VI

| Ingredient | Weight (mg) |
| --- | --- |
| Metformin hydrochloride | 500.00 |
| Dibasic Calcium Phosphate | 107.70 |
| Hydroxypropyl cellulose | 309.00 |
| Hydroxyethyl cellulose | 103.00 |
| Colloidal silicon dioxide | 5.15 |
| Magnesium stearate | 5.15 |
| Total | 1030.00 |

TABLE VII

| Ingredient | Weight (mg) |
| --- | --- |
| Metformin hydrochloride | 250.00 |
| Lactose | 70.00 |
| Hydroxypropyl cellulose | 175.00 |
| Colloidal silicon dioxide | 2.50 |
| Magnesium stearate | 2.50 |
| Total | 500.00 |

EXAMPLE 8

A directly-compressible formulation for an extended-release tablet containing 750 mg of metformin hydrochloride was prepared by mixing the ingredients set forth in Table VIII using the same procedure as in Example 1. The formulation described in Table VIII was directly compressed and monitored for weight, hardness, thickness and friability using the same apparatus and procedure as in Example 1.

TABLE VIII

| Ingredient | Weight (mg) |
| --- | --- |
| Metformin hydrochloride | 750.00 |
| Lactose | 161.55 |
| Hydroxypropyl cellulose | 463.50 |
| Hydroxyethyl cellulose | 154.50 |

TABLE VIII-continued

| Ingredient | Weight (mg) |
|---|---|
| Colloidal silicon dioxide | 7.73 |
| Magnesium stearate | 7.72 |
| Total | 1545.00 |

It is to be understood that the foregoing description is illustrative of the invention and shall not be interpreted as limiting the scope of the invention which is defined by the claims which follow.

What is claimed is:

1. An extended-release matrix formulation capable of being directly compressed into tablets comprising the ingredients:
    (a) about 30 to about 60% by weight on a dry weight basis, based on the weight of the formulation, of metformin hydrochloride having a particle size of about 150 to about 600 microns and a density in the range of about 0.6 to about 0.9 g/ml;
    one or more pharmaceutically acceptable polymers selected from the group consisting of: (i) polyethylene oxide having a number average molecular weight of about 100,000 to about 7,000,000, a particle size of about 100 to about 900 microns, a density of about 1.15 to about 1.26 g/ml and a viscosity of about 7,500 to about 10,000 centipoise at 20° C., present in an amount of about 5 to about 45% by weight on a dry weight basis, based on the weight of the formulation; (ii) hydroxypropyl cellulose having a number average molecular weight of about 80,000 to about 1,150,000, a particle size of about 170 to about 600 microns, a density of about 3.0 to about 7.0 g/ml and a viscosity of about 300 to about 3,000 centipoise at 20° C., present in an amount of about 10 to about 35% by weight on a dry weight basis, based on the weight of the formulation; (iii) hydroxyethyl cellulose having a number average molecular weight of about 75,000 to about 1,500,000, a particle size of about 50 to about 250 microns, a density of about 0.2 to about 0.9 g/ml and a viscosity of about 3,500 to about 5,500 centipoise at 20° C., present in an amount of about 10 to about 20% by weight on a dry weight basis, based on the weight of the formulation; and (iv) ethyl cellulose having a particle size of about 1 to about 10 microns, a density of about 0.1 to about 0.8 g/ml and a viscosity of about 5 to about 15 centipoise at 20° C., present in an amount of about 5 to about 20% by weight on a dry weight basis, based on the weight of the formulaton;
    (c) about 5 to about 40% by weight on a dry weight basis, based on the weight of the formulation, of a pharmaceutically acceptable insoluble filler;
    (d) about 0.1 to about 3% by weight on a dry weight basis, based on the weight of the formulation, of a pharmaceutically acceptable glidant; and
    (e) about 0.1 to about 3% by weight on a dry weight basis, based on the weight of the formulation, of a pharmaceutically acceptable lubricant.

2. The formulation of claim 1 wherein the filler is selected from the group consisting of pharmaceutically acceptable: (a) lactose having a particle size of about 20 to about 400 microns and a density of about 0.3 to about 0.9 g/ml; (b) dibasic calcium phosphate having a particle size of about 75 to about 425 microns and a density of about 0.5 to about 1.5 g/ml; (c) microcrystalline cellulose having a particle size of about 20 to about 300 microns and a density of about 0.2 to about 0.7 g/ml; (d) calcium sulfate having a particle size of about 1 to about 200 microns and a density of about 0.6 to about 1.3 g/ml; and mixtures thereof.

3. The formulation of claim 1 wherein the glidant comprises colloidal silicon dioxide having a density of about 0.029 to about 0.040 g/ml.

4. The formulation of claim 1 wherein the lubricant comprises magnesium stearate having a particle size of about 450 to about 550 microns and a density of about 1.00 to about 1.80 g/ml.

5. The formulation of claim 1 further comprising an antidiabetic agent selected from the group consisting of sulfonylureas; α-glucosidase inhibitors; glitazones and combinations of two or more of the foregoing antidiabetic agents.

6. A tablet formed from the formulation of claim 1.

7. The tablet of claim 6 wherein the tablet contains about 100 mg to about 800 mg of metformin hydrochloride in unit dosage form.

8. The tablet of claim 7 wherein the tablet contains about 250 mg to about 750 mg of metformin hydrochloride in unit dosage form.

9. A compressed, extended-release tablet containing about 100 mg to about 800 mg of metformin hydrochloride in unit dosage form comprising the ingredients:
    (a) about 30 to about 60% by weight on a dry weight basis, based on the weight of the tablet, of metformin hydrochloride having a particle size of about 150 to about 600 microns and a density in the range of about 0.6 to about 0.9 g/ml;
    (b) one or more pharmaceutically acceptable polymers selected from the group consisting of: (i) polyethylene oxide having a number average molecular weight of about 100,000 to about 7,000,000, a particle size of about 100 to about 900 microns, a density of about 1.15 to about 1.26 g/ml and a viscosity of about 7,500 to about 10,000 centipoise at 20° C., present in an amount of about 5 to about 45% by weight on a dry weight basis, based on the weight of the tablet; (ii) hydroxypropyl cellulose log a number average molecular weight of about 80,000 to about 1,150,000, a particle size of about 170 to about 600 microns, a density of about 3.0 to about 7.0 g/ml and a viscosity of about 300 to about 3,000 centipoise at 20° C., present in an amount of about 10 to about 35% by weight on a dry weight basis, based on the weight of the tablet; (iii) hydroxyethyl cellulose having a number average molecular weight of about 75,000 to about 1,150,000, a particle size of about 50 to about 250 microns, a density of about 0.2 to about 0.9 g/ml and a viscosity of about 3,500 to about 5,500 centipoise at 20° C., present in an amount of about 10 to about 20% by weight on a dry weight basis, based on the weight of the tablet; and (iv) ethyl cellulose having a particle size of about 1 to about 10 microns, a density of about 0.1 to about 0.8 g/ml and a viscosity of about 5 to about 15 centipoise at 20° C., present in an amount of about 5 to about 20% by weight on a dry weight basis, based on the weight of the tablet;
    (c) about 5 to about 40% by weight on a dry weight basis, based on the weight of the tablet, of a pharmaceutically acceptable insoluble filler;
    (d) about 0.1 to about 3% by weight on a dry weight basis, based on the weight of the tablet, of a pharmaceutically acceptable glidant; and (e) about 0.1 to about 3% by weight on a dry weight basis, based on the weight of the tablet, of a pharmaceutically acceptable lubricant.

10. The tablet of claim 9 wherein the filler is selected from the group consisting of pharmaceutically acceptable: (a) lactose having a particle size of about 20 to about 400 microns and a density of about 0.3 to about 0.9 g/ml; (b) dibasic calcium phosphate having a particle size of about 75 to about 425 microns and a density of about 0.5 to about 1.5 g/ml; (c) microcrystalline cellulose having a particle size of about 20 to about 300 microns and a density of about 0.2 to about 0.7 g/ml; (d) calcium sulfate having a particle size of about 1 to about 200 microns and a density of about 0.6 to about 1.3 g/ml; and mixtures thereof.

11. The tablet of claim 9 wherein the glidant comprises colloidal silicon dioxide having a density of about 0.029 to about 0.040 g/ml.

12. The tablet of claim 9 wherein the lubricant comprises magnesium stearate having a particle size of about 450 to about 550 microns and a density of about 1.00 to about 1.80 g/ml.

13. The tablet of claim 9 further comprising an antidiabetic agent selected from the group consisting of sulfonylureas; α-glucosidase inhibitors; glitazones and combinations of two or more of the foregoing antidiabetic agents.

14. The tablet of claim 9 wherein the metformin hydrochloride is present in unit dosage form in an amount of about 250 mg to about 750 mg.

15. A direct compression process for preparing an extended-release tablet containing about 100 mg to about 800 mg of metformin hydrochloride in unit dosage form which comprises the steps of:
(a) blending the following ingredients:
(1) about 30 to about 60% by weight on a dry weight basis, based on the weight of the tablet, of metformin hydrochloride having a particle size of about 150 to about 600 microns and a density in the range of about 0.6 to about 0.9 g/ml;
(2) one or more pharmaceutically acceptable polymers selected from the group consisting of: (i) polyethylene oxide having a number average molecular weight of about 100,000 to about 7,000,000, a particle size of about 100 to about 900 microns, a density of about 1.15 to about 1.26 g/ml and a viscosity of about 7,500 to about 10,000 centipoise at 20° C., present in an amount of about 5 to about 45% by weight on a dry weight basis, based on the weight of the tablet; (ii) hydroxypropyl cellulose having a number average molecular weight of about 80,000 to about 1,150,000, a particle size of about 170 to about 600 microns, a density of about 3.0 to about 7.0 g/ml and a viscosity of about 300 to about 3,000 centipoise at 20° C., present in an amount of about 10 to about 35% by weight on a dry weight basis, based on the weight of the tablet; (iii) hydroxyethyl cellulose having a number average molecular weight of about 75,000 to about 1,150,000, a particle size of about 50 to about 250 microns, a density of about 0.2 to about 0.9 g/ml and a viscosity of about 3,500 to about 5,500 centipoise at 20° C., present in an amount of about 10 to about 20% by weight on a dry weight basis, based on the weight of the tablet; and (iv) ethyl cellulose having a particle size of about 1 to about 10 microns, a density of about 0.1 to about 0.8 g/ml and a viscosity of about 5 to about 15 centipoise at 20°, present in an amount of about 5 to about 20% by weight on a dry weight basis, based on the weight of the tablet;
(3) about 5 to about 40% by weight on a dry weight basis, based on the weight of the tablet, of a pharmaceutically acceptable insoluble filler;
(4) about 0.1 to about 3% by weight on a dry weight basis, based on the weight of the tablet, of a pharmaceutically acceptable glidant; and
(5) about 0.1 to about 3% by weight on a dry weight basis, based on the weight of the tablet, of a pharmaceutically acceptable lubricant; and
(b) directly compressing the blend formed in step (a) to produce the tablet.

16. The process of claim 15 wherein the filler is selected from the group consisting of pharmaceutically acceptable: (a) lactose having a particle size of about 20 to about 400 microns and a density of about 0.3 to about 0.9 g/ml; (b) dibasic calcium phosphate having a particle size of about 75 to about 425 microns and a density of about 0.5 to about 1.5 g/ml; (c) microcrystalline cellulose having a particle size of about 20 to about 300 microns and a density of about 0.2 to about 0.7 g/ml; (d) calcium sulfate having a particle size of about 1 to about 200 microns and a density of about 0.6 to about 1.3 g/ml; and mixtures thereof.

17. The process of claim 15 wherein the glidant comprises colloidal silicon dioxide having a density of about 0.029 to about 0.040 g/ml.

18. The process of claim 15 wherein the lubricant comprises magnesium stearate having a particle size of about 450 to about 550 microns and a density of about 1.00 to about 1.80 g/ml.

19. The process of claim 15 further comprising mixing the metformin hydrochloride with an antidiabetic agent selected from the group consisting of sulfonylureas; α-glucosidase inhibitors; glitazones and combinations of two or more of the foregoing antidiabetic agents.

20. The process of claim 15 wherein the metformin hydrochloride is present in unit dosage form in an amount of about 250 mg to about 750 mg.

* * * * *